US00PP21366P2

(12) United States Plant Patent
Parham

(10) Patent No.: US PP21,366 P2
(45) Date of Patent: Oct. 5, 2010

(54) ***CHRYSANTHEMUM* PLANT NAMED 'FOXY TIME'**

(50) Latin Name: *Chrysanthemum morifolium*
Varietal Denomination: Foxy Time

(75) Inventor: Ruth Parham, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 12/386,720

(22) Filed: Apr. 22, 2009

Related U.S. Application Data

(60) Provisional application No. 61/125,190, filed on Apr. 23, 2008.

(51) Int. Cl.
*A01H 5/00* (2006.01)

(52) U.S. Cl. ..... Plt./295

(58) Field of Classification Search ..... Plt./295
See application file for complete search history.

(56) References Cited

U.S. PATENT DOCUMENTS

PP15,121 P2 8/2004 Bergman

*Primary Examiner*—Annette H Para
(74) *Attorney, Agent, or Firm*—Phase M, LLP

(57) ABSTRACT

A new variety of *Chrysanthemum* plant named 'Foxy Time', having blushed orange red quills with golden yellow spoon tip anemone flowers. The plants have a tidy compact habit with good foliage.

1 Drawing Sheet

Botanical classification: *Chrysanthemum morifolium.*

Variety denomination: The new *Chrysanthemum* variety denomination is 'Foxy Time'.

BACKGROUND OF THE INVENTION

The present invention comprises a new and distinct cultivar of *Chrysanthemum* botanically known as *Chrysanthemum morifolium,* and referred to by the cultivar name 'Foxy Time'.

'Foxy Time', identified as 22824-0, originated from a cross made in a controlled breeding program in Chichester, West Sussex, United Kingdom.

The female parent of the new variety is '21718-0' an undistributed, unpatented seedling, and the male parent is '22033-0' an undistributed, unpatented seedling.

The new variety 'Foxy Time' has been asexually reproduced by vegetative cuttings in Chichester, West Sussex, United Kingdom and the distinguishing characteristics are retained through successive generations of asexual reproduction.

BRIEF SUMMARY OF THE INVENTION

'Foxy Time' is a pot type of *Chrysanthemum* plant variety having golden yellow spoon tip with blushed orange red quill anemone flowers.

Comparison with Female Parent

Plants of the new *Chrysanthemum* variety 'Foxy Time' are dissimilar to the female parent '21718-0' in plant habit and growth rate. In side-by-side comparisons in Chichester, West Sussex, United Kingdom, under commercial practice, plants of the new *Chrysanthemum* variety 'Foxy Time' differed from plants of the female parent '21718-0' in the following characteristics:

1. The new variety 'Foxy Time' produces golden yellow spoon tipped anemone flowers whereas the female parent '21718-0' produces yellow anemone flowers.

2. Plants of the new variety 'Foxy Time' have larger and taller inflorescence than plants of the female parent '21718-0'.
3. Plants of the new variety 'Foxy Time' have shorter response time than plants of the female parent '21718-0'.

Comparison with Male Parent

Plants of the new *Chrysanthemum* variety 'Foxy Time' are dissimilar to the male parent '22033-0' in plant habit and growth rate. In side-by-side comparisons in Chichester, West Sussex, United Kingdom, under commercial practice, plants of the new *Chrysanthemum* variety 'Foxy Time' compared with plants of the male parent '22033-0' in the following characteristics:

1. The new variety 'Foxy Time' produces golden yellow spoon tip anemone flowers whereas the male parent '22033-0' produces red single spoon flowers.
2. Plants of the new variety 'Foxy Time' are similar size inflorescence to the plants of the male parent '22033-0'.
3. Plants of the new variety 'Foxy Time' have shorter response time than plants of the male parent '22033-0'.

Comparison with Graceland Honey

Plants of the new *Chrysanthemum* variety 'Foxy Time' are dissimilar to plants of the variety 'Graceland Honey', U.S. Plant Pat. No. 15,121, in plant habit and growth rate. In side-by-side comparisons in Chichester, West Sussex, United Kingdom, under commercial practice, plants of the new *Chrysanthemum* variety 'Foxy Time' differed from plants of 'Graceland Honey' in the following characteristics:

1. The new variety 'Foxy Time' produces golden yellow anemone flowers whereas 'Graceland Honey' produces orange—bronze anemone flowers.
2. Plants of the new variety 'Foxy Time' have smaller and shorter inflorescence than plants of 'Graceland Honey'.

3. Plants of the new variety 'Foxy Time' have shorter response time than plants of 'Graceland Honey'.
4. Plants of the new variety 'Foxy Time' produce anemone flowers with quill rays and spoon tips whereas 'Graceland Honey' produces anemone flowers with elongated oblong shaped rays.

BRIEF DESCRIPTION OF ILLUSTRATIONS

Typical specimens of the plant and flowers for the new *Chrysanthemum* variety 'Foxy Time' are shown in the accompanying digital photograph. The colors shown are as true as possible within the usual limits of this kind of illustration.

FIG. 1 is a whole plant view of the new variety 'Foxy Time' grown in a pot. The plant shown in the illustration and described below is 56 days from the onset of Short Days.

DETAILED BOTANICAL DESCRIPTION

The following description of the new *Chrysanthemum* variety 'Foxy Time' is of plants grown in a greenhouse in Chichester, West Sussex, United Kingdom, in the month of March. The cultivar has not been observed under all possible environmental conditions. The phenotype may vary significantly with variations in the environment such as temperature, length of day and light intensity, without any variance in genotype. The commercial classification of the new variety is a Pot *Chrysanthemum.*

Plants of the new variety have been grown successfully under temperature conditions averaging about 18° C. at night and about 24° C. to 25° C. during the day under assimilated light conditions of about 2500 lux. The plants respond well to the use of growth retardant, such as 3-4 applications of B9 with an average dosage of about 2 gram per liter. To produce a commercial product, the plants may be pinched once with the center bud removed. The typical container size for commercial growth is 1 liter. It has been observed that the shelf life of the new variety is about 28 days with a response time of about 7½ weeks. The new variety is suitable for growth in a temperature range of about 15° C. to 25° C.

The following description is with respect to a plant produced as pot *Chrysanthemum.* In the description of this new *Chrysanthemum* variety, color values have been taken from The Royal Horticultural Society Colour Chart (R.H.S.C.C.) by comparison to the new *Chrysanthemum* variety itself and may differ from the colors shown in the accompanying photograph.

Plant

Plant Type: Pot.
Habit: Upright and free branching.
Height (cm): 15.
Width (cm): 24.
Stem:
- *Length* (*cm*).—4.
- *Diameter* (*cm*).—0.4.
- *Texture.*—Slightly pubescent.
- *Color.*—138B.

Branching Characteristics: Upright and free branching.
Lateral Branches:
- *Length* (*cm*).—9.
- *Diameter* (*cm*).—0.2.
- *Texture.*—Slightly pubescent.

Number of Breaks from Pinch: 5.
Response Time: 52 days.
Vigor: Medium.
Shelf Life: 28 days.
Life of blooms: 28 days.
Disease (Susceptibility/Resistance observed): None observed to date.
Pest (Susceptibility/Resistance observed): None observed to date.
Drought and temperature (Susceptibility/Resistance observed): None observed to date.
Growth Retardant Type and Treatment: 3 applications of about 2 gm/liter B9 @ 2, 21 and 28 days after sticking unrooted cuttings. The plants were grown for two weeks in Long Day conditions (20 hours of light) and then transferred to Short Day conditions (13 hours of dark).
Propagation:
- *Type.*—Vegetative propagation via stem cuttings.
- *Time to rooting.*—14 days with soil temperatures of 18° C.
- *Rooting habit.*—After 7 Long Days, the first roots emerge and form root primordia. After 14 Long Days, a complete root system is developed.

Foliage

Number of Leaves per Lateral Branch: 9.
Compound or Single: Single.
Arrangement of Leaves: Alternate.
- *Shape of leaf.*—Typically 5 lobed.
- *Size of leaf.*—Width (cm): 5 Length (cm): 8.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Slightly pubescent. Bottom: Pubescent.

Petiole.
- *Color.*—Near 137C.
- *Length* (*cm*).—1.8.
- *Diameter* (*cm*).—0.3.
- *Surface.*—Slightly pubescent.

Venation: net, prominent lateral and mid-veins at underside.
- *Color.*—Upper side: slightly lighter than 138B under side: 138B.

Color:
- *Mature leaf, upper side.*—138A; under side: 139C.
- *Young leaf, upper side.*—137A; under side: 139C.

Flower

Flower appearance: Matte.
Flower type: Anemone.
Flower form: Slightly cupped.
Flower shape: Circular.
Flowering habit: Domed.
Number of blossoms per branch: 4.
Typical and observed flowering season: January to December.
Inflorescence form: Cyme.
- *Depth of fully expanded blossoms* (*cm*).—1.8.
- *Diameter of fully expanded blossoms* (*cm*).—6.
- *Anemone center diameter* (*cm*).—2.5.

Phyllaries:
- *Number.*—24.
- *Color.*—137D.
- *Length* (*cm*).—0.5 to 0.8.
- *Width* (*cm*).—0.1 to 0.3.
- *Texture/appearance.*—Pubescent.

Peduncle:
*Length* (*cm*).—9.
*Diameter* (*cm*).—0.2.
*Angle from stem* (*degrees*).—40.
*Color.*—138B.
*Surface.*—Slightly Pubescent.
*Habit.*—Slightly undulating.
*Strength.*—Medium.
Pedicel:
*Length.*—Terminal (cm): 3.5 lateral (cm): 4.
*Diameter* (*cm*).—0.2.
*Color.*—138B.
*Angle from the stem* (*degrees*).—40.
*Surface.*—Slightly pubescent.
*Habit.*—Slightly undulating.
*Strength.*—Medium.
Ray florets:
*Form/shape.*—Cylindrical with spoon tips.
*Texture/appearance.*—Matte.
*Number per flower.*—52.
Quill:
*Length* (*cm*).—3 Width (cm): 0.4 tapers to 0.1.
Spoon:
*Length* (*cm*).—0.3 to 1.2 Width (cm): 0.4 to 0.7.
*Apex.*—Rounded.
*Base.*—Tapered.
*Margin.*—Entire.
Disc florets:
*Form/shape.*—Cylindric.
*Texture/appearance.*—Matte.
*Number per flower.*—More than 200.
*Length* (*cm*).—1.3; Width (cm): 0.2.
*Diameter of disc* (*cm*).—3.2.
Fragrance : None
Flower Bud (at onset of color):
*Length* (*cm*).—1.
*Diameter* (*cm*).—1.
*Form/shape.*—Round.
General flower color:
1. *Ray florets, upper side.*—Immature: Spoon tips : 12A. Tube: 13C and 34C. Mature: Spoon tips : 12A. Tube: 13C and 34C. Older/Fading: Spoon tips : 12A. Tube: 13C and 34C.
2. *Ray florets, under side.*—Immature: Spoon tip and tube: 45C. Mature: 45C. Older/Fading: 45D.
3. *Ray florets, tube, outer side.*—13C.
4. *Ray florets, tube, inner side.*—12A.
5. *Disc florets.*—Immature: 12A , 42B, and a hint of 150B. Mature: 12A , 42B, and a hint of 150B. Older/Fading: 12A and 42B.
6. *Bud* (*at onset of color*).—46A.

Flower progression with age: There is no difference in flower form but there is a slight colour change with age.

Reproductive Organs

Gynoecium present on Ray and Disc florets:
Ray florets per individual flower: Pistillate.
*Pistil number.*—52.
*Stigma color.*—154A.
*Stigma shape.*—Forked.
*Style color.*—154B.
*Style length* (*cm*).—0.5.
Disc florets per individual flower: Pistillate.
*Pistil number.*—More than 200.
*Stigma color.*—154A.
*Stigma shape.*—Forked.
*Style color.*—154B.
*Style length* (*cm*).—0.5.
Androecium present on Disc florets: Staminate.
*Stamen number.*—200 approx.
*Anther shape.*—Thread.
*Anther color.*—12A.
*Pollen color.*—14A.
*Pollen quantity.*—Plenty.
Fruit and Seeds: None observed.

What is claimed is:

1. A new and distinct variety of *Chrysanthemum* plant, substantially as described and illustrated herein.

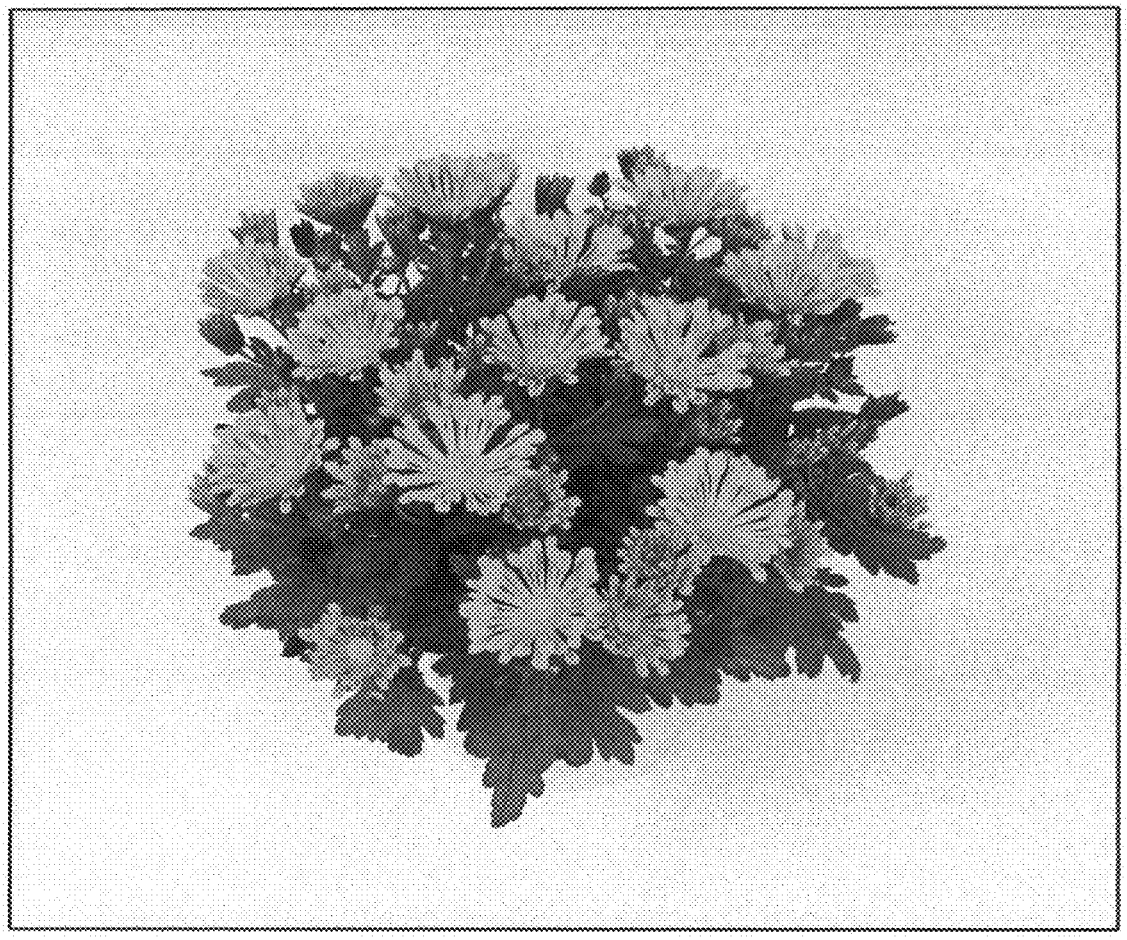

* * * * *